United States Patent
Sammartini

(10) Patent No.: US 9,423,371 B2
(45) Date of Patent: Aug. 23, 2016

(54) CAPACITANCE ELECTRODE STRUCTURE FOR MEASURING MOISTURE

(75) Inventor: Marco Sammartini, Chiasso (CH)

(73) Assignee: BRY-AIR PROKON SAGL, Chiasso (CH)

( * ) Notice: Subject to any disclaimer, the term of this patent is extended or adjusted under 35 U.S.C. 154(b) by 72 days.

(21) Appl. No.: 13/808,545

(22) PCT Filed: Jul. 6, 2010

(86) PCT No.: PCT/IB2010/001654
§ 371 (c)(1),
(2), (4) Date: Mar. 20, 2013

(87) PCT Pub. No.: WO2012/004621
PCT Pub. Date: Jan. 12, 2012

(65) Prior Publication Data
US 2013/0170093 A1 Jul. 4, 2013

(51) Int. Cl.
*G01N 27/22* (2006.01)
*G01R 27/26* (2006.01)
*G01D 5/24* (2006.01)

(52) U.S. Cl.
CPC .......... *G01N 27/223* (2013.01); *G01R 27/2605* (2013.01); *G01D 5/24* (2013.01)

(58) Field of Classification Search
CPC .. G01N 27/223; G01N 27/22; C08L 2666/04; C08L 2666/24; C08L 75/06; C08L 75/08; A01G 25/16
USPC ......... 324/663–668, 674, 675, 681, 682–690, 324/71.1; 340/602–604; 73/29.01, 335.04; 361/286
See application file for complete search history.

(56) References Cited

U.S. PATENT DOCUMENTS

| | | | | |
|---|---|---|---|---|
| 3,992,665 A | * | 11/1976 | Preikschat | 324/666 |
| 4,736,156 A | | 4/1988 | Benson et al. | |
| 5,933,015 A | * | 8/1999 | Siddiqui et al. | 324/643 |
| 6,014,029 A | * | 1/2000 | Soto et al. | 324/664 |
| 8,047,056 B2 | * | 11/2011 | Kanare | G01N 1/2273 73/29.01 |

FOREIGN PATENT DOCUMENTS

GB 717127 10/1954
WO WO 89/03527 4/1989

OTHER PUBLICATIONS

PCT Search Report and Written Opinion of the International Searching Authority for International Application No. PCT/IB2010/001654—Date of Completion of Search: Mar. 18, 2011; Date of Mailing: Apr. 1, 2011, 8 pages.

\* cited by examiner

*Primary Examiner* — Melissa Koval
*Assistant Examiner* — Felicia Farrow
(74) *Attorney, Agent, or Firm* — Locke Lord LLP

(57) ABSTRACT

Device (1) for measuring moisture of materials flowing in the shape of dried, liquid or gaseous granulates, or in the shape of powders in at least one duct disposed at least partially along an axis (X-X) through which the material of which the moisture has to be measured flows, comprising: at least one capacitor (Cx) wherein the material of which the moisture has to be measured flows, characterized in that the capacitor (CX) comprises: at least two metallic rings (3) coaxially mounted to said axis X-X and adjacent to an inner wall of the duct through which the material of which the moisture has to be measured flows; at least one dielectric element (5) having: dielectric constant substantially linear with the temperature changing, and thermal expansion lower than $\alpha=27\times10-6/°$ C.

14 Claims, 2 Drawing Sheets

CAPACITANCE ELECTRODE STRUCTURE FOR MEASURING MOISTURE

The present invention concerns with the industrial measurement of moisture and particularly, a device for measuring moisture of products processed in industrial treatments.

Apparatuses for measuring moisture are instruments adapted for measuring moisture present in a lot of substance samples and have a number of applications, being used in fact in food, chemical and pharmaceutical industries.

There are different kinds of apparatuses for measuring moisture.

WO8903527, for example, describes a portable electronic instrument for measuring moisture comprising a capacitive probe and a corresponding circuit meeting the dielectric coefficient of a probed material to obtain a signal corresponding to the moisture content. The probe further comprises a temperature probe meeting the temperature of the probed material and the circuit appears adapted for providing the temperature compensation for the obtained signal of the moisture content.

On the other hand, U.S. Pat. No. 4,736,156 describes an apparatus for measuring "in-line" the dielectric constant or the moisture percentage of a material, such as "tobacco", moving inside the pipe or chute walls. A capacitive difference is used as measure.

The apparatus is composed of a device with four electrodes, with two of the electrodes out of the pipe or chute walls and two of the electrodes attached inside the pipe or chute walls. The two inner electrodes are connected by switches to the two outer electrodes respectively, in such a way that the first and second capacitance are revealed at the output terminals of the electrode device based on the switch positions. The output terminals of the electrode device are connected to an oscillator producing an output signal indicating the oscillation frequency that is proportional with the capacitance measured at the terminals of the electrode device. The output signal of the oscillator is connected to a microprocessor used for calculating a value proportional with the changing of the electrode device capacitance when the switches are closed. This value may be used for determining the dielectric constant or the moisture percentage of the material inside the chute.

The Applicant first noticed that in some known devices the moisture measuring does not happen in-line during the manufacturing process, but by sampling and subsequent measuring.

A similar approach is very complicated, it requires long time and the measurement may not be reliable because a lot of elements caused by an incorrect sampling.

In these cases, the Applicant further observed that the sampling is not very representative of the production in progress because the laboratory systems could sample only few grams and in some manufacturing processes it is not possible to take a sample in the specific point of interest, for example in silos or dryers in nitrogen environment.

The Applicant further observed that in known systems wherein the measurement happens in-line, the measuring devices have a complexed structure rendering difficult the material flow in their inside and consequently the measurement of the material moisture.

The Applicant further observed that the complexed structure of system meters wherein the measurement happens in-line would prevent their easy installation and integration in the treatment and/or manufacturing process.

The Applicant found that the above mentioned problems could be get over with a device for measuring moisture of materials flowing in the shape of dried, liquid or gaseous granulates, or in the shape of powders adapted for detecting the capacitance changes of a capacitor comprising a plurality of rings wherein the material of which the water percentage has to be measured flows.

Therefore, in a first aspect the invention concerns with a the device for measuring moisture of materials flowing in the shape of dried, liquid or gaseous granulates, or in the shape of powders in at least one duct disposed at least partially along an axis (X-X) through which the material of which the moisture has to be measured flows, comprising:

at least one capacitor Cx wherein the material of which the moisture has to be measured flows, characterized in that the capacitor comprises:
at least three metallic ring coaxially mounted to said axis X-X and adjacent to an inner wall of the duct through which the material of which the moisture has to be measured flows;
at least one dielectric element having:
dielectric constant substantially linear with the temperature changing, and
thermal expansion lower than $\alpha=27\times10^{-6}/°$ C.

The present invention, in the afore said aspect, may present at least one of the preferred characteristics herein after described.

Preferably, said at least one dielectric elements comprises at least one ring of dielectric material having a dimension substantially correspondent with the dimension of said at least three metallic rings.

Conveniently, a radially inner surface of the metallic rings is disposed substantially aligned with the inner wall of the duct through which the material of which the moisture has to be measured flows.

Preferably, the dielectric has low hygroscopic characteristics.

Conveniently, according to an embodiment, the capacitor Cx comprises four rings of dielectric material and three metallic rings interposed between the four rings of dielectric material.

Further, the device for measuring the moisture has at least one unit for compensating the thermal expansion of said at least one dielectric element.

Preferably, the compensating unit comprises at least one elastic means and at least one sensor, disposed between at least one ring of dielectric material and a flange for supporting the capacitor.

To provide a correct measurement in-line of moisture, because the dielectric constant of water changes as temperature changes, the device for measuring moisture further comprises at least one temperature probe.

Preferably, the temperature probe is a RTD sensor.

Advantageously the capacitor is inserted in a bridge circuit.

Conveniently the bridge circuit comprises at least a first and a second electric power line parallel connected, the first line comprising at least two resistances (R1; R2) and said second line comprising at least one reference resistance (RX) and at least said capacitor (Cx).

Preferably, the bridge circuit is connected to an oscillator adapted for applying a determined variable sinusoidal signal to the bridge circuit for measuring the changes of capacitor capacitance.

Conveniently, the dielectric element is substantially realized in PTFE.

Alternatively, the dielectric element is substantially realized in ceramic material.

In addition, the inner walls of the capacitor Cx are hermetically sealed.

This renders the device able to operate in nitrogen environments too.

Further characteristics and advantages of the invention will be more evident from the detailed description of some preferred embodiments, but not exclusive, of a device for measuring moisture of materials flowing in the shape of dried, liquid or gaseous granulates, or in the shape of powders according to the present invention.

Such a description will be hereinafter explained referring to the attached drawings, provided for purposes of illustrations only, and thereby not limitative, wherein.

Figure 1:
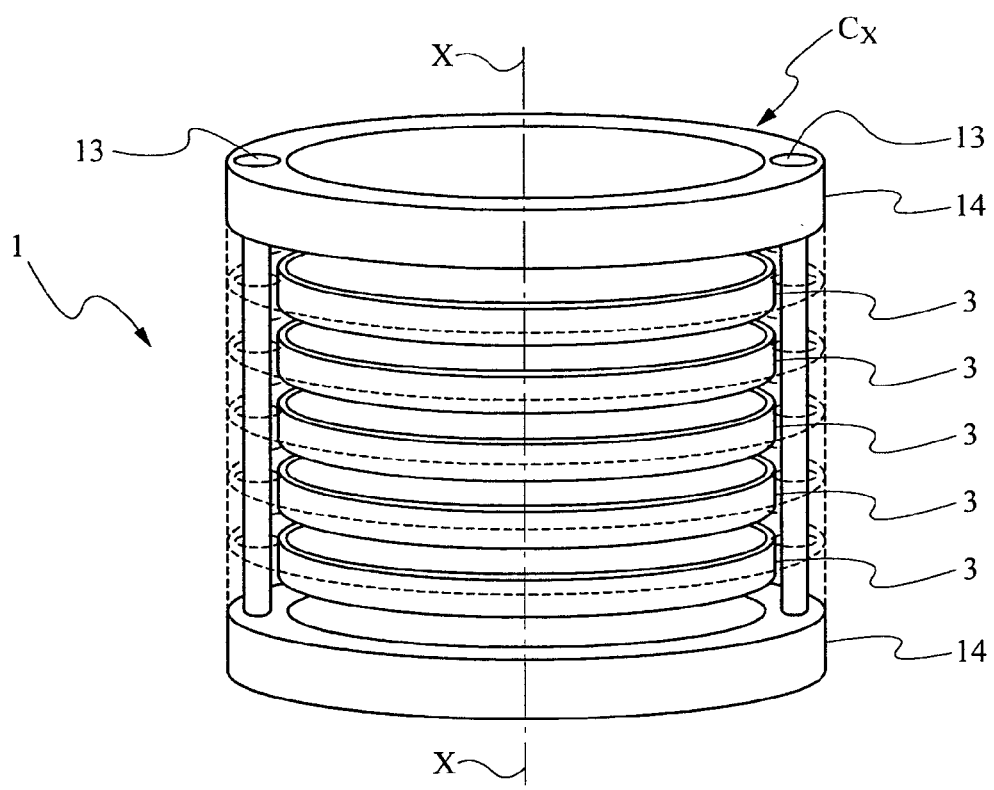
FIG. 1 is a schematic prospective view of a first embodiment of the measuring device according to the present invention.
Figure 2:
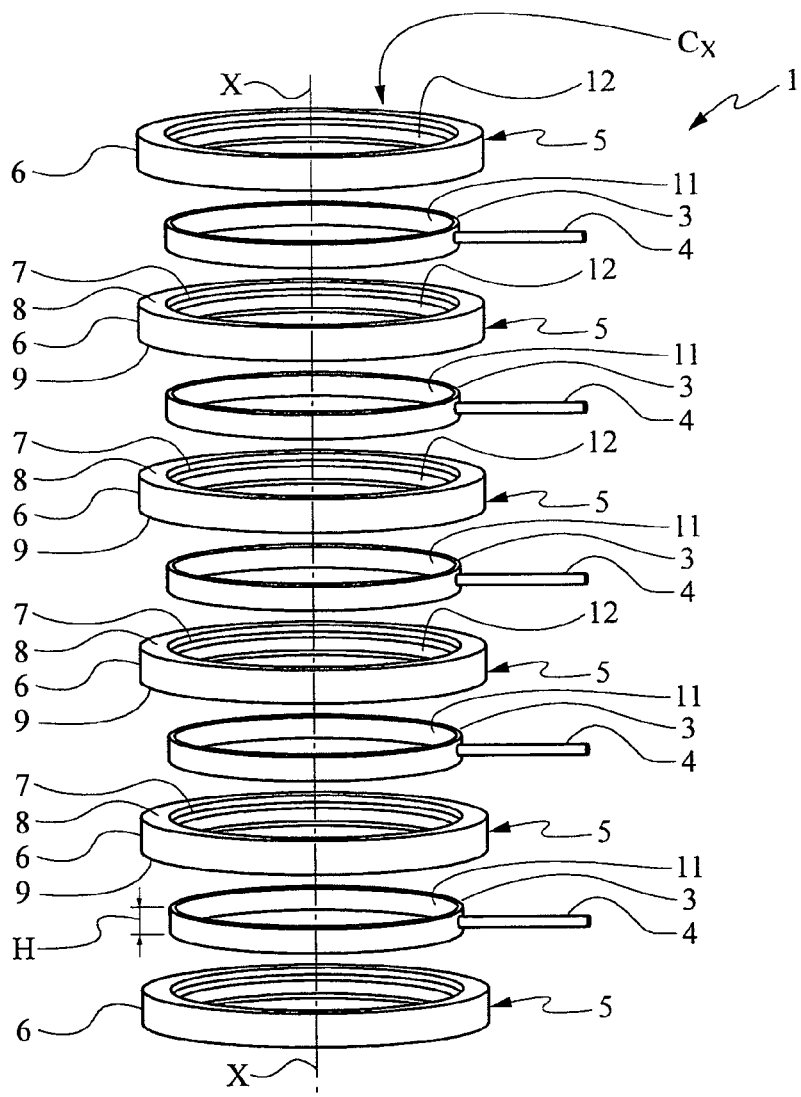
FIG. 2 is a schematic partially exploded view of the device of FIG. 1.

Referring to FIGS. 1-2, a device for measuring in-line moisture in processes wherein materials flowing in the shape of dried, liquid or gaseous granulates are treated, or in the shape of powders according to the present invention, is identified with the numeral 1.

The device 1 is adapted for its positioning in at least one duct, not shown in figures, disposed at least partially along an axis (X-X), through which the material of which the moisture has to be measured flows.

The device 1 in the embodiment shown in FIGS. 1 and 2 is provided with at least one capacitor Cx comprising:
- at least three metallic ring 3 each provided with its own terminal 4 for an electric connection; and
- at least one dielectric element 5.

In the embodiment shown in figures said at least one dielectric element 5 is represented by a ring 6 of dielectric material substantially having the same shape and dimension of the metallic rings 3 interposed between the three metallic rings.

According to an advantageous aspect of the present invention, in order that the capacitance of the capacitor Cx would be constant as much as possible independently from the moisture flowing into the duct, the dielectric material, the dielectric element 5 is composed of, is provided with a dielectric constant substantially linear as the temperature changes and it has a low thermal expansion as temperature changes.

Preferably, the dielectric material the dielectric element 5 is composed of, has a linear thermal expansion coefficient lower than $\alpha=27\times10^{-6}/°C$.

Preferably, the dielectric material the dielectric element 5 is composed of, has a dielectric constant higher or equal to 1.

In addition, the dielectric material the dielectric element 5 is composed of, has low hygroscopic characteristics and low porosity.

Preferably, the dielectric material the dielectric element 5 is composed of, has a porosity lower than 70 nm, preferably lower than 30 nm, for example equal to 20 nm, possibly tending to zero.

In addition, the inner walls of said capacitor Cx are hermetically sealed.

The dielectric element 5 may be substantially realized in ceramic material or substantially in PTFE.

The Applicant found that the afore said materials have a linear or simple polynomial behavior and thereby it is only necessary a little correction by software to keep the calculated value of capacitance of the device capacitor for measuring moisture.

The Applicant further found that it is recommended to use the PTFE for process temperatures lower than 50° C., whereas it is preferred to use ceramic materials for process temperatures higher than 50° C.

To allow the material moisture to be measured, preferable in the shape of granulates, flowing through the duct, the metallic rings 3 of the device 1 are rings mounted coaxial with the axis X-X having a substantially circumferential section.

Alternatively, the metallic rings 3 may present a different section, for example squared, elliptical and/or star-shaped, without falling out from the protection scope of the present invention.

The metallic rings 3 of the same device have preferably the same shape and dimension.

Similarly, as afore mentioned, the dielectric element 5 is composed of rings 6 of dielectric material provided with the afore mentioned characteristics, the rings having substantially circular section too and diameter substantially corresponding to the diameter of the metallic rings 3.

In detail, in the embodiment shown in figures, the metallic rings 3 are composed of a metallic thin sheet closed to form a ring.

Preferably, the metallic sheet has a height h comprised between 3 mm and 25 mm, ends included.

In addition, the metallic sheet may have a thickness s comprised between 0.7 mm and 5 mm, ends included.

To cover the metallic rings 3, each dielectric ring has an annular inner seat 7 adapted for housing at least partially a metallic ring 3.

The annular seats 7 of two rings 6 of dielectric material adjacent in direction X-X substantially house completely a metallic ring 3.

Advantageously, to adapt the measuring device 1 to different ducts, the device 1 according to the present invention presents a modular structure allowing metallic ring 3 and rings of dielectric material 6 to be added.

For such an object, each ring of dielectric material 6 has in the axial direction X-X a substantially annular higher flat surface 8 and a second lower flat surface 9 substantially corresponding to the former for shape and dimension and spaced therefrom in the axial direction X-X of a measure equal to the height of the ring 6 of dielectric material 3.

With the measuring device 1 assembled, each higher flat surface 8 of a ring of dielectric material 6 is abutted onto the lower flat surface 9 of the ring of dielectric material 6 adjacent in the axial direction X-X.

Advantageously, the device is mounted in a duct wherein the material of which the moisture has to be measured flows, so that said at least three metallic rings 3 are adjacent to an inner wall of the duct.

In detail, the radially inner surface 11 of the metallic rings 3 is disposed substantially aligned in the axial direction X-X with the inner wall of the duct, not shown in figure.

Preferably, the radially inner surface 11 of the metallic rings 3 is disposed substantially aligned in the axial direction X-X with the inner wall of the duct so that the inner wall 11 of the metallic rings 3 and the inner wall of the duct (not shown in figure) are substantially flush.

Preferably, also the radially inner surface 12 of the rings of dielectric material 6 is disposed substantially aligned in the axial direction X-X with the inner wall of the duct, not shown in figure.

Preferably, the radially inner surface 12 of the metallic rings 3 is disposed substantially aligned in the axial direction X-X with the inner wall of the duct so that the inner wall of the rings of dielectric material 6 and the inner wall of the duct are substantially flush.

In the preferred embodiment shown in FIGS. 1 and 2, the device 1 is composed of five metallic rings 3 and six rings of dielectric material 6, each metallic ring 3 being interposed between two metallic rings 3.

The metallic rings 3 and the rings of dielectric material 6 are assembled by two restraining annular flanges 14 and convenient assembling screws 13, two in the embodiment shown in figures, angularly spaced along the ring perimeter.

To compensate the eventual thermal expansion, the device 1 for measuring moisture comprises at least one unit 15 for compensating the thermal expansion.

Preferably, it has at least one compensating unit 15 for assembling screw 13.

Figure 3:
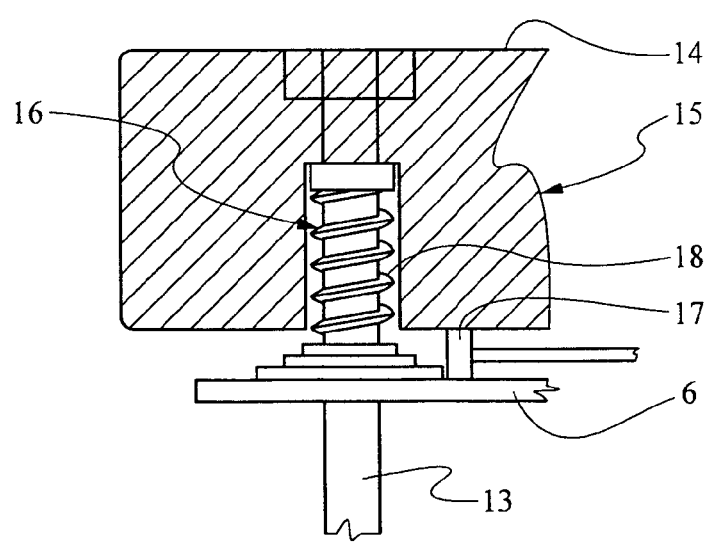
FIG. 3 is a schematic partially sectioned view of the compensation unit of the measuring device according to the present invention.

In the embodiment shown in FIG. 3 the compensating unit 15 is composed of at least one elastic means 16 and at least one sensor 17.

The elastic means 16, represented by a helical spring 18 operating by compression, is inserted on an assembling screw 13 at an end thereof and it is placed between at least a ring of dielectric material 6 and an annular flange 14.

The sensor 17 provides information from a controlling processor to correct the dielectric constant detected from the passing of material of which the moisture has to be measured as a function of the detected thermal expansion.

Because the temperature is very important in the operating principle of the device 1, because the dielectric constant changes as the temperature changes, the device according to the present invention has at least one temperature probe, not shown in figure, adapted for detecting the processing temperature and sending a signal to a controlling processor, not shown, for correcting the dielectric constant and subsequently the detected moisture.

Preferably, the temperature probe is a RTD sensor, normally available on the market.

According to a second particularly advantageous aspect, the capacitor is inserted in a bridge circuit 29.

Figure 4:
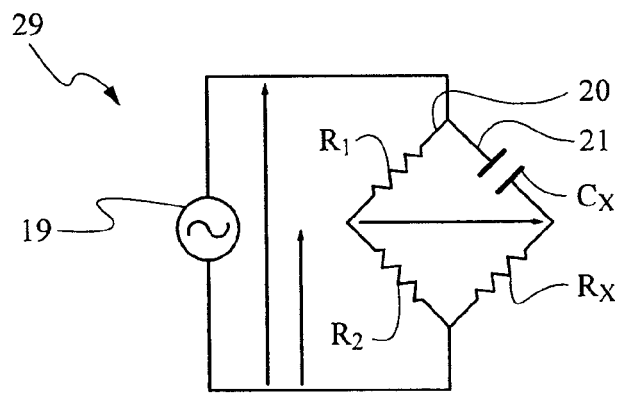
FIG. 4 is a schematic view of an embodiment of the bridge circuit of the measuring device according to the present invention.

An example of such a bridge circuit 29 is schematically represented in FIG. 4 wherein it can be seen that the bridge circuit 29 has at least a first 20 and a second 21 electric power line parallel connected.

The first line 20 comprises at least two resistances R1; R2 connected in series, whereas the second line comprises at least one reference resistance RX connected in series to the capacitor Cx.

Preferably, the bridge circuit 29 is connected in parallel to an oscilloscope 19 adapted for applying a determined variable sinusoidal signal to the bridge circuit 29 for measuring the changes of capacitance of the capacitor Cx.

The device for measuring the moisture according to the present invention is able to measure the changing of capacitor capacitance, relatively to a reference value, of a material, in the shape of dried, liquid or gaseous granulates, or in the shape of powders, flowing in its inside. In detail, the changes of capacitance of the capacitor Cx of a material flowing inside the metallic rings 3 and the rings 6 of dielectric material, relatively to a reference value.

The reference value is the capacitance value provided by the same completely dried material flowing in the device, and it is a function of the dielectric constant of the completely dried material.

After the first measurement with the completely dried material it is possible to carry out directly in-line the measurement of moisture that will be a function of the capacitance changes of the capacitor Cx.

The capacitance change of capacitor Cx changes as the dielectric constant of material flowing in the capacitor inside changes relatively to the value of dielectric constant of the same completely died material.

Particularly, in addition to other considerations such as for example the material temperature and the possible thermal expansion, the dielectric constant changes as the number of water dipoles comprised in the material flowing in the capacitor Cx changes.

Then, through the change of capacitance of the capacitor Cx relatively to a reference value and an appropriate processing by a controlling processor, not shown, it is possible to measure the moisture percentage of the material flowing through the capacitor itself.

The present invention has been described referring to some embodiments. To the embodiments herein represented in detail may be made various modifications, anyway remaining in the protection scope of the invention, defined by the following claims.

The invention claimed is:

1. Device (1) for measuring moisture of materials flowing in the shape of dried, liquid or gaseous granulates, or in the shape of powders in at least one duct disposed at least partially along the axis (X-X) through which the material of which the moisture has to be measured flows, comprising: at least one capacitor (Cx) having a hollow cylindrical shape through which the material of which the moisture has to be measured flows, characterized in that the capacitor (CX) comprises: at least two metallic rings (3) coaxially mounted to said axis (X-X) and adjacent to an inner wall of the duct through which the material of which the moisture has to be measured flows; at least one dielectric element (5) and a second dielectric element (5), each having: dielectric constant substantially linear with the temperature changing, and thermal expansion lower than $\alpha = 27 \times 10^{-6}/°$ C.; said at least one dielectric element (5) and said second dielectric element (5) each comprising a ring (6) of dielectric material having an annular inner seat (7) adapted for housing at least partially one of said metallic rings (3); said annular seats (7) of said two rings (6) of dielectric material adjacent in direction of said axis (X-X))substantially housing completely said one of said metallic rings (3), hermetically sealing inner walls of said capacitor (Cx); and said two rings (6) of dielectric material adjacent in direction of said axis (X-X) and said one of said metallic rings (3), forming a modular structure allowing said one of said metallic rings (3) and said two rings (6) of dielectric material to he added to adapt the measuring device (1) to different ducts.

2. Device (1) for measuring moisture according to claim 1, wherein a radially inner surface of said electrodes is disposed substantially aligned with said inner wall of said at least one duct.

3. Device (1) for measuring moisture according to claim 1, wherein said dielectric element (5) has low hygroscopic characteristics.

4. Device (1) for measuring moisture according to claim 1, wherein said capacitor (Cx) comprises four rings of dielectric material (6) and three metallic rings (3) interposed between the four rings of dielectric material (6).

5. Device (1) for measuring moisture according to claim 1, further comprising at least one unit (15) for compensating the thermal expansion of the dielectric material.

6. Device (1) for measuring moisture according to claim 5, wherein said compensating unit (15) comprises at least one elastic means (16) and at least one sensor (17) disposed between at least one ring of dielectric material (6) and a flange for supporting the capacitor (Cx).

7. Device (1) for measuring moisture according to claim 1, further comprising at least one temperature probe.

8. Device (1) for measuring moisture according to claim 1, characterized in that said capacitor (Cx) is inserted in a bridge circuit (29).

9. Device (1) for measuring moisture according to claim 8, wherein said bridge circuit (29) comprises at least a first (20) and a second (21) electric power line parallel connected, the first line (20) comprising at least two resistances (R1; R2) and said second line (21) comprising at least one reference resistance (RX) and at least said capacitor (Cx).

10. Device (1) for measuring moisture according to claim 8, wherein said bridge circuit (29) is connected to an oscillator (19) adapted for applying a variable sinusoidal signal to said bridge circuit (29) for measuring changes of capacitance of said capacitor (Cx).

11. Device (1) for measuring moisture according to claim 1, wherein said at least one dielectric element is substantially composed of PTFE.

12. Device (1) for measuring moisture according to claim 1, wherein said dielectric element (5) is substantially composed of ceramic material.

13. Device (1) for measuring moisture according to claim 1, wherein the inner walls of said capacitor (Cx) are hermetically sealed.

14. Device (1) for measuring, moisture of materials flowing in the shape of dried, liquid or gaseous granulates, or in the shape of powders in at least one duct disposed at least partially along the axis (X-X) through which the material of which the moisture has to be measured flows, comprising: at least one capacitor (Cx) having a hollow cylindrical shape through which the material of which the moisture has to be measured flows, characterized in that the capacitor (CX) comprises: at least two metallic rings (3) coaxially mounted to said axis (X-X) and adjacent to an inner wall of the duct through which the material of which the moisture has to be measured flows; at least one dielectric element (5) and a second dielectric element (5), each having: dielectric constant substantially linear with the temperature changing, and thermal expansion lower than $\alpha=27 \times 10^{-6}/°$ C.; and at least one unit (15) for compensating the thermal expansion of the dielectric material; said at least one dielectric element (5) and said second dielectric element (5) each comprising a ring (6) of dielectric material having an annular inner seat (7) adapted for housing at least partially one of said metallic rings (3); said annular seats (7) of said two rings (6) of dielectric material adjacent in direction of said axis (X-X) substantially housing completely said one of said metallic rings (3), hermetically sealing inner walls of said capacitor (Cx); and said two rings (6) of dielectric material adjacent in direction of said axis (X-X) and said one of said metallic rings (3) forming a modular structure allowing said one of said metallic rings (3) and said two rings (6) of dielectric material to be added to adapt the measuring device (1) to different ducts.

* * * * *